(12) United States Patent
Kandori et al.

(10) Patent No.: US 10,620,101 B2
(45) Date of Patent: Apr. 14, 2020

(54) DUROMETER

(71) Applicant: MAXELL, LTD., Kyoto (JP)

(72) Inventors: Akihiko Kandori, Tokyo (JP); Yuko Sano, Tokyo (JP); Yuhua Zhang, Tokyo (JP); Shigemitsu Ando, Kyoto (JP); Mitsunobu Watanabe, Kyoto (JP); Mitsuo Okimoto, Tokyo (JP)

(73) Assignee: MAXELL, LTD., Kyoto (JP)

( * ) Notice: Subject to any disclaimer, the term of this patent is extended or adjusted under 35 U.S.C. 154(b) by 174 days.

(21) Appl. No.: 15/737,543

(22) PCT Filed: Apr. 6, 2016

(86) PCT No.: PCT/JP2016/061231
§ 371 (c)(1),
(2) Date: Dec. 18, 2017

(87) PCT Pub. No.: WO2016/208253
PCT Pub. Date: Dec. 29, 2016

(65) Prior Publication Data
US 2018/0172569 A1 Jun. 21, 2018

(30) Foreign Application Priority Data
Oct. 27, 2015 (JP) .................................. 2015-210979

(51) Int. Cl.
*G01N 3/38* (2006.01)
*G01N 3/42* (2006.01)
(Continued)

(52) U.S. Cl.
CPC ............. *G01N 3/38* (2013.01); *A61B 5/0053* (2013.01); *A61B 5/442* (2013.01); *G01N 1/34* (2013.01);
(Continued)

(58) Field of Classification Search
CPC .. G01N 3/38; G01N 3/36; G01N 3/34; G01N 3/40; G01N 3/42; G01N 2203/0003;
(Continued)

(56) References Cited

U.S. PATENT DOCUMENTS

| 4,646,571 A | 3/1987 | Kising et al. |
| 5,911,694 A | 6/1999 | Ikeda et al. |
| 2018/0177448 A1* | 6/2018 | Zhang .................... A61B 5/442 |

FOREIGN PATENT DOCUMENTS

| JP | 61-240140 A | 10/1986 |
| JP | H10-062328 A | 3/1998 |

(Continued)

OTHER PUBLICATIONS

International Search Report for WO 20161208253 A1, dated May 24, 2016.

*Primary Examiner* — Lisa M Caputo
*Assistant Examiner* — Rose M Miller
(74) *Attorney, Agent, or Firm* — Volpe and Koenig, P.C.

(57) ABSTRACT

An object of the present invention is to provide a durometer enabling a contact portion in contact with an object to perform smooth piston motion. The durometer includes a main body unit including a movable unit pressed continuously against an object to be measured, a first sensor outputting acceleration information corresponding to an acceleration of movement of a contact part of the object to be measured in contact with the movable unit in a pressing direction, a second sensor outputting reactive force information corresponding to a reactive force at the contact part of the object to be measured in contact with the movable unit, a motor, a crank mechanism driven by the motor and causing the main body unit and the movable unit to perform piston motion, and at least one buffering member disposed on a periphery of the main body unit.

19 Claims, 14 Drawing Sheets

(51) Int. Cl.
*A61B 5/00* (2006.01)
*G01N 3/40* (2006.01)
*G01N 1/34* (2006.01)

(52) U.S. Cl.
CPC .............. *G01N 3/40* (2013.01); *G01N 3/42* (2013.01); *A61B 2562/0223* (2013.01); *G01N 2203/0676* (2013.01)

(58) Field of Classification Search
CPC ... G01N 2203/0032; G01N 2203/0037; G01N 2203/0042; G01N 2203/0048; G01N 2203/0076; G01N 2203/0078; G01N 2203/0082; G01N 2203/0087; G01N 2203/03; G01N 2203/0676; G01N 2203/2203; A61B 5/0053; A61B 5/442; A61B 2562/0223
USPC ............................................ 73/573, 574, 576
See application file for complete search history.

(56) References Cited

FOREIGN PATENT DOCUMENTS

| | | |
|---|---|---|
| JP | 2001-212087 A | 8/2001 |
| JP | 2003-156146 A | 5/2003 |
| JP | 2012-154260 A | 8/2012 |

\* cited by examiner

DUROMETER

TECHNICAL FIELD

The present invention relates to a durometer.

BACKGROUND ART

Conventionally, measuring hardness of an object has been useful in many cases. When an object is a human body, measuring hardness of the human body is useful in the medical field or the fields of dermatological surgery and cosmetic surgery. For example, in the medical field, measuring the hardness of a given part allows for a medical diagnosis such as ulcers on the skin surface of a bed-ridden patient who has suffered from an ulcer as a result of having been in bed in the same position for a long period, skin edema caused by a change of an internal organ, scleroderma, and so forth. Also, in the fields of dermatological surgery and cosmetic surgery, measuring the hardness of a given part makes it possible to determine progress of a disease and an effect of a drug therapy.

For example, a conventional tactile sensor, which acquires information on a change in a resonance state caused when a mechanical vibration part comes in contact with an object and which outputs the acquired information as hardness information of the object, has been known (see Patent Document 1).

Further, a conventional technique for reciprocating a piston by use of a crank mechanism (see Patent Document 2) has been known, and a conventional technique for sealing a piston assembly (see Patent Document 3) has also been known.

RELATED ART DOCUMENTS

Patent Documents

Patent Document 1: Japanese Patent Application Laid-Open Publication No. H10-062328
Patent Document 2: Japanese Patent Application Laid-Open Publication No. 2012-154260
Patent Document 3: Japanese Patent Application Laid-Open Publication No. 2003-156146

SUMMARY OF THE INVENTION

Problems to be Solved by the Invention

For example, it is assumed that information from an acceleration sensor is used in a durometer measuring hardness of an object. When the acceleration sensor is used, it is required to make a contact portion in contact with the object perform smooth piston motion such that noise is not mixed in the information acquired from the sensor.

A technique of Patent Document 1 utilizes information on a change in the resonance state caused when the mechanical vibration part comes in contact with the object and in the first place, is not a technique utilizing the acceleration sensor. Accordingly, the durometer in which the acceleration sensor is used needs a configuration in which the contact portion in contact with the object performs smooth piston motion.

Patent Document 2 discloses a technique by which piston motion is performed by use of the crank mechanism. According to such a technique, movement of a crack shaft eccentric to a shaft of a power unit (motor, etc.) is converted into piston motion. As a result, the contact portion in contact with the object shakes laterally. This shaking motion causes noise to be mixed in the information from the acceleration sensor. For this reason, it has been considered that applying the crack mechanism to the durometer in which the acceleration sensor is used is difficult.

Also, Patent Document 3 discloses a technique by which the piston is sealed. In this technique, only reduction in mechanical load applied to a tip portion of the piston has been taken into consideration. Thus, a sealing technique enabling smooth piston motion in the durometer in which the acceleration sensor is used has not been studied so far.

In this regard, an object of the present invention is to provide a durometer enabling a contact portion in contact with an object to perform smooth piston motion.

Means for Solving the Problems

For example, in order to solve the above problems, configurations described in Claims are adopted. The present application includes a plurality of means solving the above problems, and by way of example, there is provided a durometer including a main body unit including a movable unit pressed continuously against an object to be measured, a first sensor outputting acceleration information corresponding to an acceleration of movement of a contact part of the object to be measured in contact with the movable unit in a pressing direction, a second sensor outputting reactive force information corresponding to a reactive force at the contact part of the object to be measured in contact with the movable unit, a motor, a crank mechanism driven by the motor and causing the main body unit and the movable unit to perform piston motion, and at least one buffering member disposed on a periphery of the main body unit.

Also, according to another example, there is provided a durometer including a main body unit including a movable unit pressed continuously against an object to be measured, a first sensor outputting acceleration information corresponding to an acceleration of movement of a contact part of the object to be measured in contact with the movable unit in a pressing direction, a second sensor outputting reactive force information corresponding to a reactive force at the contact part of the object to be measured in contact with the movable unit, a motor, a crank mechanism driven by the motor and causing the main body unit and the movable unit to perform piston motion, at least one buffering member disposed on a periphery of the main body unit, and a contact member encircling a periphery of the movable member and in contact with the object to be measured, the contact member including a cutout.

Also, according to still another example, there is provided a contact member for a durometer including a movable unit pressed continuously against an object to be measured. The contact member is configured in such a way as to encircle a periphery of the movable unit and come in contact with the object to be measured, and includes a cutout.

Effects of the Invention

According to the present invention, in a durometer, a contact portion in contact with an object can perform smooth piston motion. Further characteristics of the present invention will be apparent from the description of the present specification and the accompanying drawings. Also, other problems, configurations, and advantageous effects will be apparent from the description of the following embodiments.

BRIEF DESCRIPTIONS OF THE DRAWINGS

FIG. 6(a) is a waveform diagram indicating voltage from the magnetic sensor;

FIG. 6(b2) is a waveform diagram indicating acceleration waveform based on output from the acceleration sensor;

FIG. 6(c) is a waveform diagram indicating displacement of the object;

DETAILED DESCRIPTION OF PREFERRED EMBODIMENTS

Figure 1:
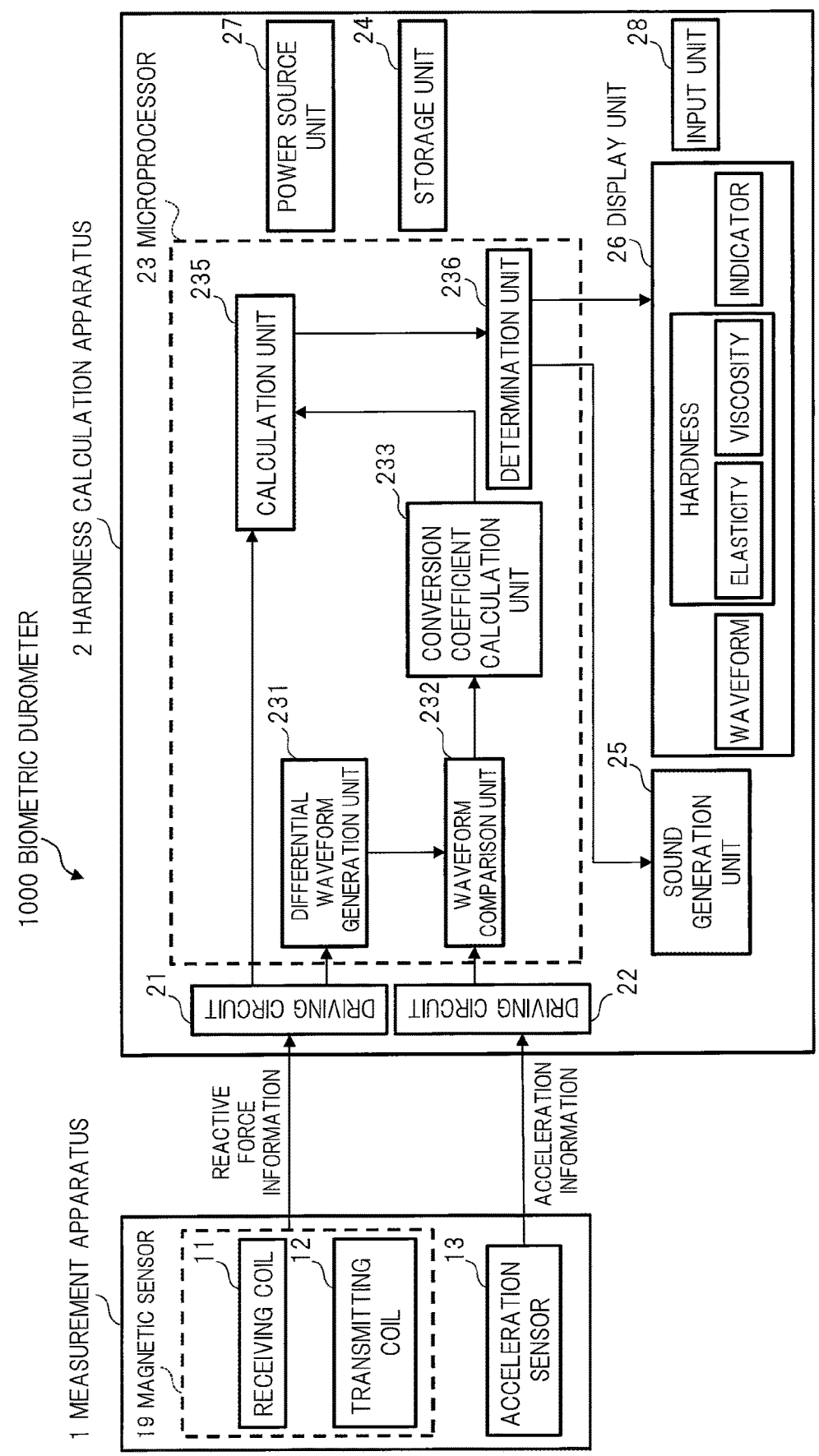
FIG. 1 is an overall configuration diagram of a biometric durometer according to an embodiment.

Hereinafter, embodiments of the present invention will be described with reference to the drawings. Note that specific embodiments according to the principle of the present invention are illustrated in the accompanying drawings, but these are provided for the purpose of understanding the present invention and not used to interpret the present invention in a limited way. Also, the common configurations in each of the drawings may be denoted by the same reference characters. In the following description, different units, such as V (bolt) and mV (millimeter volt), may be adopted for convenience of description or illustration.

The following embodiments relate to a technique for calculating hardness of an object to be measured. In the following description, a living body such as human body is taken as an example of the object to be measured. The object to be measured is, however, not limited to the living body. For example, a durometer according to the following embodiments may be applied also to an object other than the living body.

Hardness is an index indicating how hard an object to be measured is. Hardness can be indicated as various types of indexes. By way of example, hardness may be defined by a conception including at least either elasticity or viscosity. Elasticity represents such a property that the object deformed by an applied force tries to return to its original state when the force is removed. Viscosity represents such a property that the object deformed by an applied force is hard to return to its original state.

FIG. 1 is an overall configuration diagram of a biometric durometer. A biometric durometer 1000 includes a measurement apparatus 1 and a hardness calculation apparatus 2. Note that parts of the configuration are omitted in the measurement apparatus 1 in FIG. 1, compared to the measurement apparatus 1 in each of FIGS. 2 and 3.

The configuration and an operation principle of the measurement apparatus 1 will be described, referring to FIG. 1 as well as FIGS. 2 and 3. The measurement apparatus 1 includes a main body unit 14 having a receiving coil 11 (magnetic field detecting means), a movable unit 15 having a transmitting coil 12 (magnetic field generating means) and an acceleration sensor 13, and a spring 16 (resilient member). Note that a combination of the receiving coil 11 and the transmitting coil 12 is referred to as a magnetic sensor 19. The magnetic sensor 19 outputs reactive force information corresponding to a reactive force generated at a contact part of the object in contact with the movable unit 15. The acceleration sensor 13 outputs acceleration information corresponding to the acceleration of movement of the movable unit 15 in a pressing direction at the contact part of the object in contact with the movable unit 15.

A contact portion 20 of the movable unit 15 is a portion pressed against a trunk B of a human body, which is the object, in such a way as to dent the trunk B at hardness calculation. Note that the main body unit 14 and the movable unit 15 have rigidity. The acceleration sensor 13 detects information of the acceleration of the movement in the pressing direction. The trunk B has a spring-like property and a dashpot-like property. For example, it is assumed that the trunk B has a spring 17(a) (spring constant K) and a dashpot 17(b) (dashpot constant G). The spring constant K corresponds to an elasticity component of the trunk B, and the dashpot constant G corresponds to a viscosity component of the trunk B. At least one of the elasticity component and the viscosity component is a subject of calculation carried out in this embodiment.

The magnetic sensor 19 outputs information of a voltage corresponding to a magnitude of the reactive force of the trunk B in response to a pressure applied to the trunk B by the measurement apparatus 1. To allow the magnetic sensor 19 to function in this manner, the receiving coil 11 and the transmitting coil 12 are disposed to be opposed to each other. Also, the spring 16 with a (known) spring constant K' is disposed between the main body unit 14 and the movable unit 15 (see FIG. 2). Note that the spring 16 should be selected such that a relation K'>K is satisfied. Otherwise, when a pressing force F is applied to the main body unit 14 (see FIG. 2), the main body unit 14 and the movable unit 15 come in contact with each other at the contact portion 20, and as a result, the function of the magnetic sensor 19 is impaired. For example, the measurement apparatus 1 may be designed such that a distance D between the main body unit 14 and the movable unit 15 is substantially 2 mm and a compression amount of the spring 16 is substantially 0.5 mm when the pressing force F is applied to the main body unit 14.

The spring 16 may be replaced with a spring having the same shape and a larger wire diameter. Also, a free length of the spring 16 may be increased. When the spring 16 having such a configuration is adopted, a larger pressing force F is needed to cause the spring 16 to be compressed by the same amount of compression. As a result, a larger force is applied to the object from the main body unit 14. Accordingly, hardness of a part in a deep layer of the object can be measured. Conventionally, hardness has been measured only at the skin surface, and this poses a problem that information on a deeper layer of the skin cannot be acquired. In contrast, the above configuration enables measurement of not only the hardness of the skin surface but also the hardness in a range from the skin surface to the subcutaneous tissue, the muscle, etc., in the deeper layer of the skin.

Then, operations of the magnetic sensor 19 and peripheral components around the magnetic sensor 19 will be described with reference to FIG. 2. First, an AC oscillation source 31 generates an AC voltage having a specific frequency (e.g., 20 kHz). The generated AC voltage is converted by an amplifier 32 into an AC current having a specific frequency, and the converted AC current flows through the transmitting coil 12. The AC current flowing through the oscillation coil 12 generates a magnetic field, which generates an induced electromotive force at the receiving coil 11.

The induced electromotive force generates an AC current (with the same frequency as the frequency of the AC voltage generated by the AC oscillation source 31) at the receiving coil 11. The generated AC current is amplified by a preamplifier 33, and a signal after the amplification is input to a detection circuit 34. The detection circuit 34 detects the signal after the amplification using the specific frequency or a double frequency of the specific frequency generated by the AC oscillation source 31. For the detection, an output from the AC oscillation source 31 is introduced into a reference signal input terminal of the detection circuit 34 as a reference signal 35. An operation method using a full-wave rectifier circuit instead of using the detection circuit 34 may be employed. Voltage information (output signal) from the detection circuit 34 (or the rectifier circuit) passes through a low-pass filter 36 and is introduced to a driving circuit 21 (see FIG. 1) of the hardness calculation apparatus 2.

Figure 4:
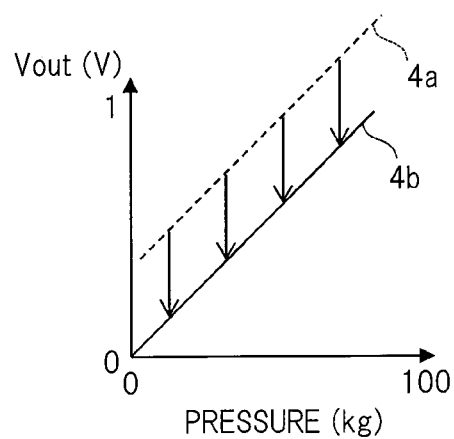
FIG. 4 is a graph indicating a relation between output voltage from a receiving coil and pressure caused by a pressing force.

Note that the relation between the pressure (force F) applied to the main body unit 14 and a magnitude of the voltage expressed by the output signal introduced from the low-pass filter 36 to the driving circuit 21 is as illustrated by a line 4a (broken line) in FIG. 4. The line 4a extends linearly because the spring constant K' of the spring 16 is large and the amount of compression of the spring 16 in response to the pressure to the main body unit 14 is small. Even if a relation between the pressure (force F) and the output signal introduced to the driving circuit 21 is not proportional, such a relation is converted so as to have a linear characteristic, and the linear relation illustrated in FIG. 4 is calculated. By correcting the line 4a to a line 4b (solid line) such that the voltage becomes zero when the pressure is zero, the relation between the pressure and the voltage may have a proportional relation passing through an origin. The above correction can be carried out by, for example, a microprocessor 23, which will be described later. Also, a conversion coefficient indicating a ratio of the pressure applied to the trunk B to the voltage information output by the magnetic sensor 19 will hereinafter be referred to as voltage/pressure conversion coefficient ($C_{mp}$ [N/mV]), which is experimentally calculated in advance.

Then, the hardness calculation apparatus 2 will be described, referring back to FIG. 1. The hardness calculation apparatus 2 is a computer apparatus. The hardness calculation apparatus 2 includes driving circuits 21 and 22, the microprocessor 23, a storage unit 24, a sound generation unit 25, a display unit 26, a power source unit 27, and an input unit 28.

The driving circuit 21 receives voltage information sent from the receiving coil 11 of the measurement apparatus 1 through the low-pass filter 36 (see FIG. 2), etc., and transmits the voltage information to the microprocessor 23. The driving circuit 22 receives acceleration information sent from the acceleration sensor 13 of the measurement apparatus 1, and transmits the acceleration information to the microprocessor 23.

The microprocessor 23 is realized by, for example, a CPU (Central Processing Unit). The microprocessor 23 includes a differential waveform generation unit 231, a waveform comparison unit 232, a conversion coefficient calculation unit 233, a calculation unit 235, and a determination unit 236. These processing units of the microprocessor 23 can be realized by various programs. For example, various programs stored in the storage unit 24 are loaded into a memory (not illustrated) of the hardness calculation apparatus 2. The microprocessor 23 executes a program loaded into the memory. Processing contents executed by the processing units of the microprocessor 23 will be described below with reference to FIGS. 5 and 6.

Figure 5:
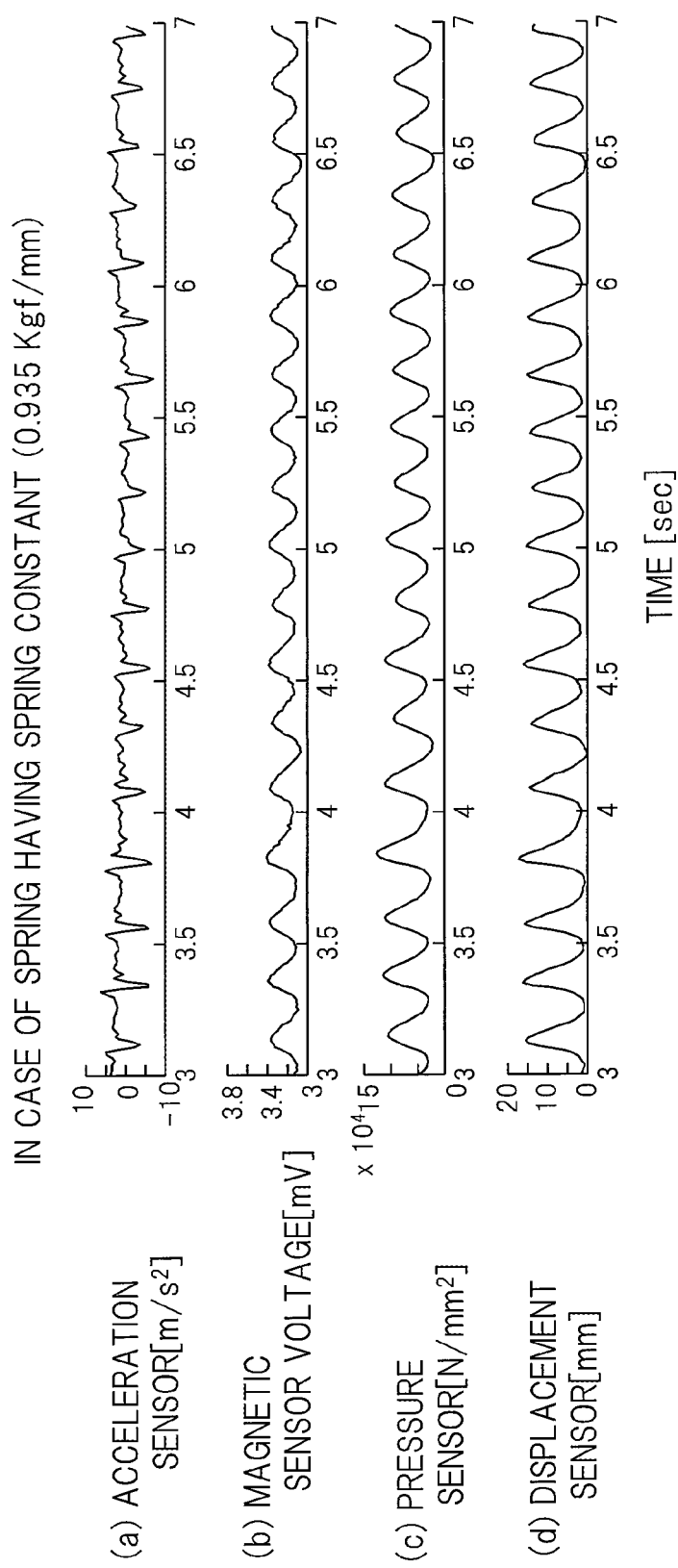
FIG. 5(a) is a waveform diagram indicating output from an acceleration sensor when an object is a spring.
FIG. 5(b) is a waveform diagram indicating output from a magnetic sensor when the object is the spring.
FIG. 5(c) is a waveform diagram indicating output from a pressure sensor when the object is the spring.
FIG. 5(d) is a waveform diagram indicating output from a displacement sensor when the object is the spring.

As illustrated in FIG. 5, when a spring with a spring constant of 0.935 kgf/mm is used, an output of the acceleration sensor 13 is as indicated in (a), an output of the magnetic sensor 19 is as indicated in (b), an output of a pressure sensor (not illustrated) used in place of the magnetic sensor 19 is as indicated in (c), and an output (true value (correct value) of displacement) of a displacement sensor (not illustrated) such as a laser sensor is, as a reference, as indicated in (d).

Figure 2:
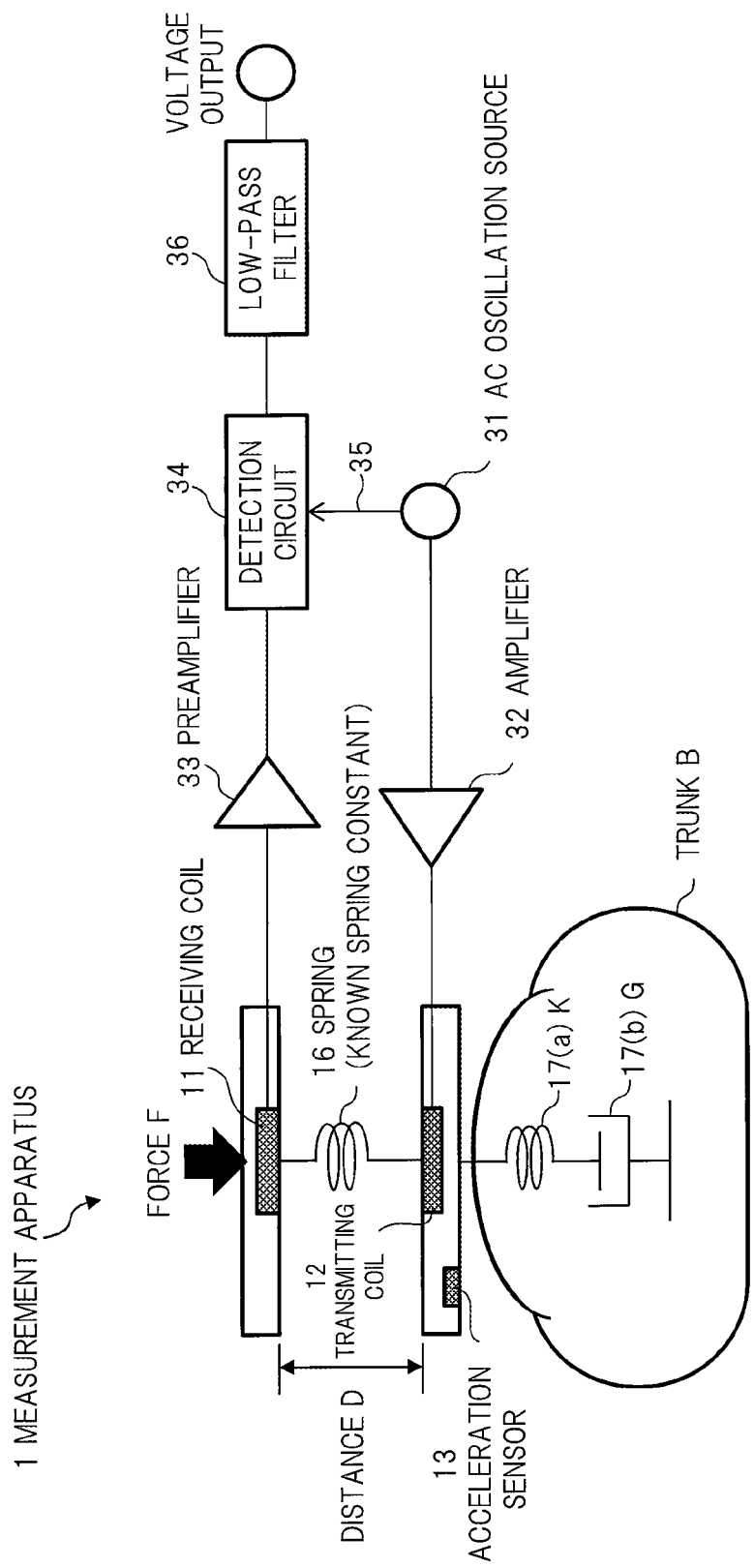
FIG. 2 is an explanatory diagram of an operation principle of a measurement apparatus.
Figure 3:
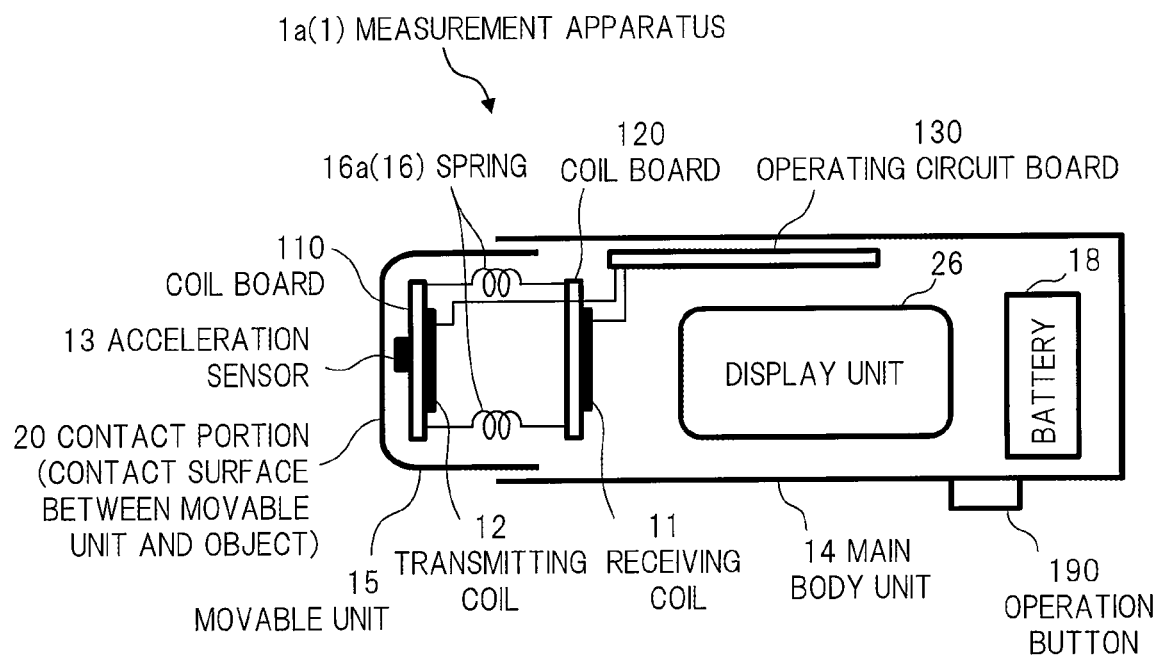
FIG. 3 is a schematic view of an example of a structure of the measurement apparatus.

An object of the present embodiment is to calculate the hardness of the object, that is, to calculate at least one of the spring constant K and the dashpot constant G in FIG. 2. To achieve this, it is first necessary to acquire information as close as possible to output information indicated in (d) by using at least one of pieces of output information indicated in (a), (b), and (c) of FIG. 5. Then, the hardness of the object is calculated by using the acquired information.

In other words, to calculate the hardness characteristics of the object without using a displacement sensor such as a laser sensor, information provided by the acceleration sensor 13 and the magnetic sensor 19 (or pressure sensor) is used. Reasons that the displacement sensor is not used are, for example, that using the displacement sensor is difficult in some circumstances, depending on surface condition of the object or whether the sensor can be fixed to the object, and that the displacement sensor is expensive.

In FIG. 5, comparing the waveform of the output from the magnetic sensor 19 indicated in (b) with the waveform of the output from the displacement sensor indicated in (d), both waveforms are different in unit on the vertical axis and amplitude, while they are similar in shape and are identical in frequency. Accordingly, by multiplying the waveform of the output from the magnetic sensor 19 indicated in (b) by a given conversion coefficient (which will hereinafter be referred to as "voltage/displacement conversion coefficient ($C_{md}$ [mm/mV])"), information of a waveform approximate to the waveform of the output from the displacement sensor indicated in (d) can be obtained. The voltage/displacement conversion coefficient $C_{md}$ is a numerical value indicating a ratio of a magnitude of an acceleration waveform to a magnitude of a second-order differential waveform (which will be described in detail later). Note that this process of approximation is similarly applicable to the waveform of the output from the pressure sensor indicated in (c) with respect to the waveform of the output from the displacement sensor indicated in (d).

Here, calculation of the hardness of the object will be described using mathematical formulas (see the drawings as needed). When the amount of compression (amount of displacement) of the spring 17(a) and the dashpot 17(b) caused by the pressing force (pressure) F applied to the main body unit 14 is denoted as X (see FIG. 2) and an output voltage from the magnetic sensor 19 is denoted as $V_m$, the following equations (1), (2), and (3) are established. Note that, as a result of the law of action and reaction, the force (pressure) F is applied also to the contact portion 20 between the movable unit 15 and the trunk B.

[Mathematical Formula 1]

$$F = K \times X \quad \text{Equation (1)}$$

$$X = C_{md} \times V_m \quad \text{Equation (2)}$$

$$F = C_{mp} \times V_m \quad \text{Equation (3)}$$

Equation (1) is an equation representing the Hooke's law. Equation (2) is an equation indicating that the amount of displacement X can be obtained by multiplying the output voltage $V_m$ from the magnetic sensor 19 by the voltage/displacement conversion coefficient $C_{md}$. Equation (3) is an equation indicating that the pressure F can be obtained by multiplying the output voltage $V_m$ from the magnetic sensor 19 by a voltage/pressure conversion coefficient $C_{mp}$.

Then, substituting Equations (2) and (3) for Equation (1) and simplifying the resulting equation yields the following Equation (4).

[Mathematical Formula 2]

$$K = \frac{C_{mp}}{C_{md}} \quad \text{Equation (4)}$$

Equation (4) indicates that a complex elastic modulus of the object can be calculated by dividing the voltage/pressure conversion coefficient $C_{mp}$ by the voltage/displacement conversion coefficient $C_{md}$. In this embodiment, this complex elastic modulus is used as information on the hardness.

Referring back to FIG. 1, the storage unit 24 is means storing various pieces of information and is realized by, for example, a RAM (Random Access Memory), a ROM (Read Only Memory), an HDD (Hard Disk Drive), etc. The storage unit 24 stores in advance the voltage/displacement conversion coefficient $C_{mp}$ calculated through an experiment.

The sound generation unit 25 is means generating a sound and is realized by, for example, a speaker. The sound generation unit 25 generates a beeping sound at the start and the end of measurement by the measurement apparatus 1, for example.

The display unit 26 is means displaying various data and is realized by, for example, an LCD (Liquid Crystal Display) or CRT (Cathode Ray Tube) display. The display unit 26 displays various waveforms, the hardness of the object (e.g., at least one of elasticity information and viscosity information), and an indicator visualizing the hardness of the object.

The power source unit 27 is power supply means in the hardness calculation apparatus 2. The input unit 28 is means operated by a user for inputting various pieces of information and is realized by, for example, a keyboard, a mouse, etc.

An example of a structure of the measurement apparatus 1 will be described with reference to FIG. 3. Matters described with reference to FIG. 2 will be appropriately omitted. A measurement apparatus 1a(1) is a pencil shape as a whole. The measurement apparatus 1a(1) includes the main body unit 14 and the movable unit 15.

The main body unit 14 includes the receiving coil 11, a coil board 120 having the receiving coil 11 mounted, an operating circuit board 130 connected to the receiving coil 11 and the transmitting coil 12, a battery 18, an operation button 190 to be operated at the start of hardness calculation, etc., and the display unit 26. The movable unit 15 has the transmitting coil 12, the acceleration sensor 13, and a coil board 110 having the transmitting coil 12 and the acceleration sensor 13 mounted.

A spring 16a(16) is disposed between the coil board 110 and the coil board 120, and the number of the spring 16a(16) is one, two, three, or four. In a simple mode, a single spring 16a(16) can be used, and a diameter of the spring 16a(16) is equal to or larger than a diameter of each coil of the coil board 110 and the transmitting coil 12. The configuration in which the single spring 16a(16) is used allows each coil of the coil board 110 and the transmitting coil 12 to be disposed inside the spring 16a(16), thereby enabling miniaturization of the measurement apparatus.

According to the measurement apparatus 1a(1), when the movable unit 15 is pressed against the object in such a way as to dent the object, the spring 16a(16) is compressed to cause the transmitting coil 12 and the receiving coil 11 to approach each other. This increases a magnitude of a magnetic field detected by the receiving coil 11. As a result, information of a voltage corresponding to a magnitude of a reactive force generated at the contact portion 20 is output from the receiving coil 11. Also, since the measurement apparatus 1a(1) is a pencil shape as a whole, it is compact and is easy to use.

Figure 7:
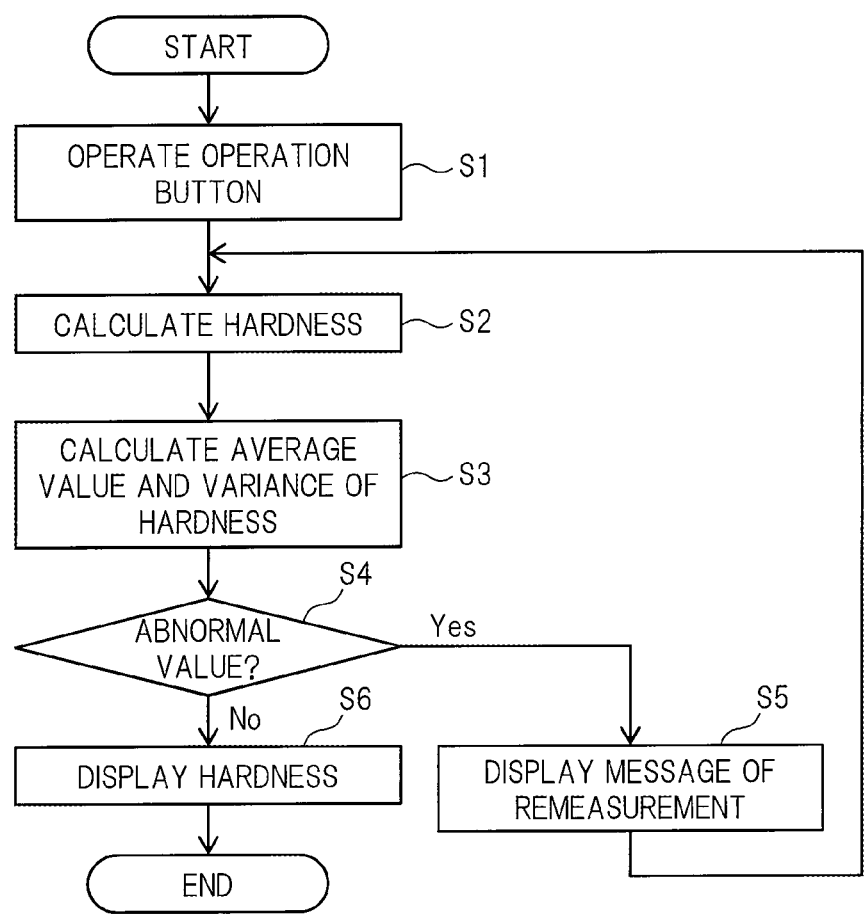
FIG. 7 is an example of a flowchart illustrating the overall flow of a processing by the biometric durometer.

Then, a process of the biometric durometer 1000 will be described with reference to a flowchart of FIG. 7 (see other drawings as needed).

First, an operator operates the operation button 190 of the measurement apparatus 1 (step S1). In this step, the whole of the measurement apparatus 1a(1) is attached to a motor not illustrated. In this configuration, by driving the motor, it is possible to press the movable unit 15 against the object continuously at a given frequency fHz.

The microprocessor 23 of the hardness calculation apparatus 2 acquires information from the measurement apparatus 1 every time the movable unit 15 of the measurement apparatus 1 is pressed against the object. Based on the information (reactive force information and acceleration information) acquired from the measurement apparatus 1, the microprocessor 23 calculates the hardness (e.g., complex elastic modulus) (step S2). Then, the microprocessor 23 calculates an average value and a variance of the hardness data calculated at step S2 (step S3).

Subsequently, the microprocessor 23 determines whether the average value and the variance calculated at step 3 are abnormal values (step 4). This process is executed by the determination unit 236 of the microprocessor 23. When the determination is Yes, the process proceeds to step S5. When the determination is No, the process proceeds to step S6. Note that determination whether the average value and the variance are abnormal values can be made by comparing the average value and the variance with a present threshold, for example.

When the determination is Yes at step S4 (when the values are abnormal), the microprocessor 23 causes the display unit 26 to display a message of remeasurement, and the process returns to step S2 (step S5).

When the determination is No at step S4, the microprocessor 23 causes the display unit 26 to display information on the hardness (step S6), and the process ends. In this embodiment, the movable unit 15 of the measurement apparatus 1 is pressed against the object a plurality of times, and accordingly, a plurality of pieces of information on the hardness can be acquired through the calculation at step S2. By way of example, the display unit 26 may display the average value of information on the hardness and the average value of information on the elasticity component.

Then, the calculation of the hardness (step S2) will be described with reference to FIG. 6. An example of calculating the complex elastic modulus as the hardness will be described below. Note that acquisition of a plurality of pieces of information on the hardness has been described in FIG. 7. In the following example, however, one round of calculation of the hardness will be described.

The microprocessor 23 acquires a voltage waveform based on voltage information sent from the magnetic sensor 19 through the driving circuit 21, and an acceleration waveform based on acceleration information sent from the acceleration sensor 13 through the driving circuit 22. The voltage waveform is input to the differential waveform generation unit 231. The acceleration waveform is input to the waveform comparison unit 232. FIG. 6(a) indicates the voltage waveform. Also, FIG. 6(b2) indicates the acceleration waveform.

Then, the differential waveform generation unit 231 differentiates the voltage waveform twice to generate a second-order differential waveform. FIG. 6(b1) indicates the second-order differential waveform calculated from the voltage waveform.

Subsequently, the waveform comparison unit 232 compares the second-order differential waveform (FIG. 6(b1)) calculated by the differential waveform generation unit 231 with the acceleration waveform (FIG. 6(b2)), and outputs the result of the comparison to the conversion coefficient calculation unit 233. Base on the comparison result, the conversion coefficient calculation unit 233 calculates the voltage/displacement conversion coefficient $C_{md}$. The conversion coefficient calculation unit 233 outputs the calculated voltage/displacement conversion coefficient $C_{md}$ to the calculation unit 235.

Figure 6:
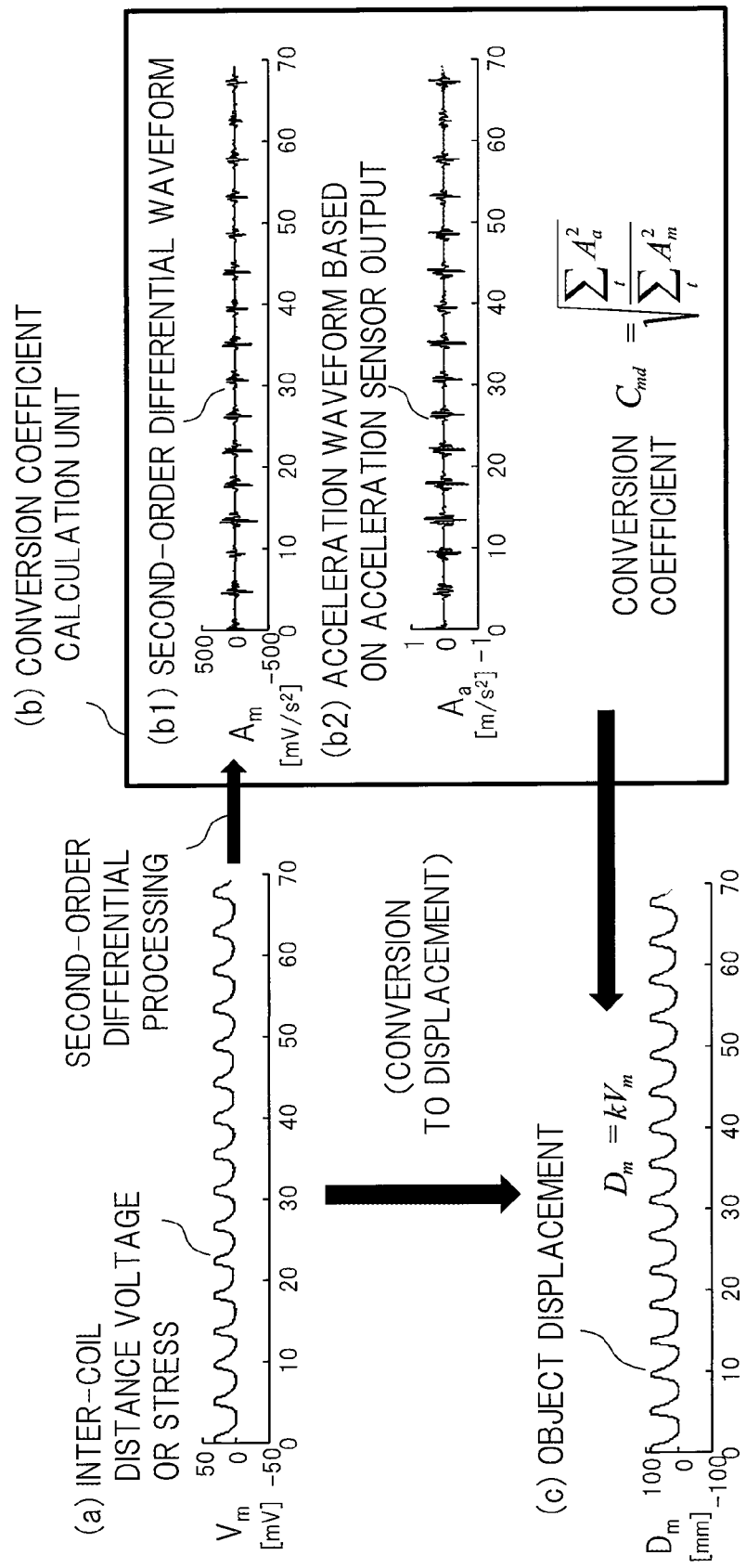
FIG. 6(b1) is a waveform diagram indicating a second-order differential waveform.

Specifically, for example, the voltage/displacement conversion coefficient $C_{md}$ can be calculated by use of the following Equation (5) (see FIG. 6(b)). Am and Aa in the equation (5) correspond to a voltage value and an acceleration value indicated in FIG. 6(b1) and FIG. 6(b2), respectively.

[Mathematical Formula 3]

$$C_{md} = \sqrt{\frac{\sum_t A_a^2}{\sum_t A_m^2}}$$

Equation (5)

Subsequently, the calculation unit 235 divides the voltage/pressure conversion coefficient $C_{mp}$ stored in the memory unit 24 in advance by the voltage/displacement conversion coefficient $C_{md}$ (see Equation (4)) to calculate the absolute value K of the complex elastic modulus of the object. The complex elastic modulus is a value of a dynamic physical property of a material of an object to be measured, taken into consideration missing energy in the form of heat upon deforming and recovering. The real part of the complex elastic modulus is equivalent to a storage modulus, and the imaginary part of the complex elastic modulus is equivalent to a loss modulus.

In the above embodiment, an example in which the complex elastic modulus is calculated as the hardness has been described. Hardness calculation is, however, not limited to this example. In another example, at least one piece of information of an elasticity component and a viscosity component may be calculated as more detailed information of the hardness. By way of example, a phase difference between the acceleration waveform and the second-order differential waveform calculated from the voltage waveform is calculated, and then, information of each of the elasticity component and the viscosity component may be calculated by use of the complex elastic modulus and the phase difference.

Embodiments relating to a structure of the measurement apparatus 1 of the biometric durometer 1000 described above will hereinafter be described.

[First Embodiment]

Figure 8:
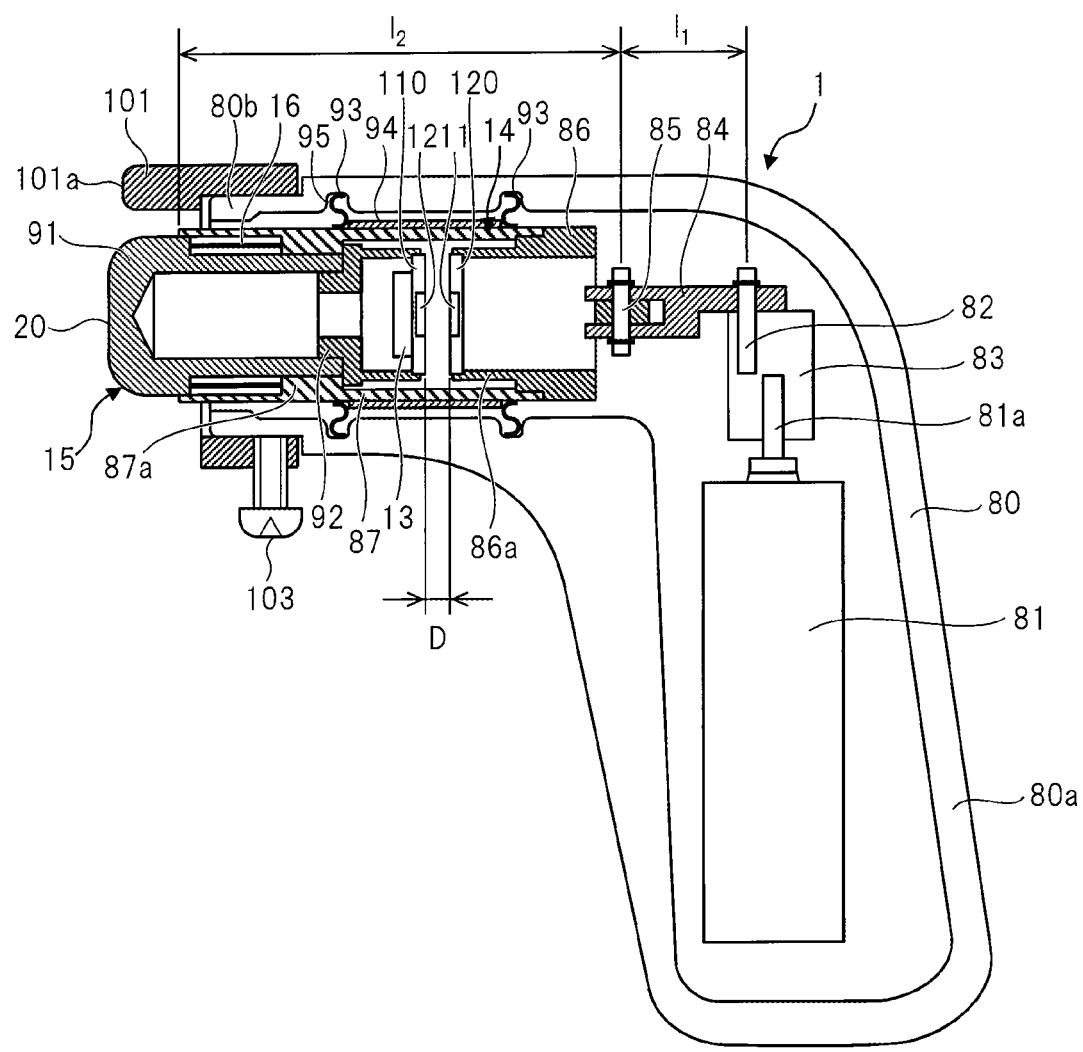
FIG. 8 is a configuration diagram of a biometric durometer according to a first embodiment.

FIG. 8 is a configuration diagram of a biometric durometer according to a first embodiment. FIG. 8 mainly illustrates constituent elements of the measurement apparatus 1 and does not illustrate constituent elements of the hardness calculation apparatus 2. The hardness calculation apparatus 2 may be incorporated into the measurement apparatus 1 of FIG. 8 or may be realized by another computer apparatus connected to the measurement apparatus 1 with or without a wire.

The measurement apparatus 1 includes a motor 81 and a crank mechanism driven by the motor 81. The crank mechanism includes a crank shaft 82 located eccentric to a shaft 81a of the motor 81, and a link (connecting member) 84 connecting the crank shaft 82 to the main body unit 14. The measurement apparatus 1 is configured such that the measurement apparatus 1 transmits power from the motor 81 to the main body unit 14 through the crank mechanism to press the movable unit 15 against the object at a given frequency.

More specifically, the structure of the measurement apparatus 1 will be described. The measurement apparatus 1 includes a housing 80 housing various constituent elements described below. In a plan view of FIG. 8, the housing 80 has a shape that is bent almost at a right angle. The housing 80 includes a first portion 80a and a second portion 80b. The first portion 80a has the motor 81 disposed therein, and the second portion 80b has the main body unit 14 disposed therein. In a bent portion between the first portion 80*a* and the second portion 80*b* of the housing 80, the crank mechanism is disposed. According to this configuration, when the motor 81 disposed in the first portion 80*a* is driven, the crank mechanism enables the main body unit 14 and the movable unit 15 to perform piston motion.

Moreover, according to this configuration, the operator is able to direct the second portion 80*b* at the object, holding the first portion 80*a* by hands. In this manner, the biometric durometer of the present embodiment has the configuration which does not require the object to be measured to stand absolutely still and which is preferably applicable to an object to be measured with motion, such as human body.

Figure 9:
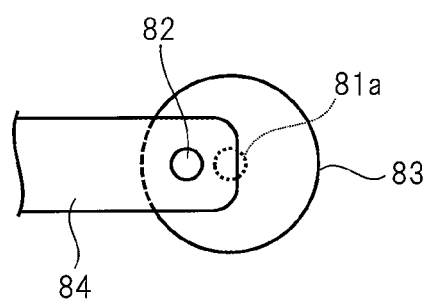
FIG. 9 is a top view of a bearing member and a crank shaft in the measurement apparatus.

The shaft 81*a* of the motor 81 is attached to a cylindrical bearing member 83. The crank shaft 82 is attached to the bearing member 83 at a position eccentric to the shaft 81*a* of the motor 81. FIG. 9 is a top view of the bearing member 83 and the crank shaft 82. Also, to further stabilize rotation of the shaft 81*a*, the bearing member 83 may have a bearing fixed around the shaft 81*a*.

The crank shaft 82 is connected to the main body unit 14 via the link 84. According to this configuration, when the motor 81 is driven, the crank shaft 82 located eccentric to the shaft 81*a* of the motor 81 rotates around the shaft 81*a* of the motor 81 in a plan view of FIG. 9. This rotation of the crank shaft 82 causes the link 84 to move in a right and left direction in FIG. 8, and as a result, the main body unit 14 and the movable unit 15 perform the piston motion. In the following description, a direction of the piston motion of the main body unit 14 and the movable unit 15 is referred to as a moving direction.

Note that a length $l_1$ of the link 84 is preferably ⅓ or more of a length $l_2$ of the main body unit 14 in the moving direction. In this configuration, it is possible to reduce a lateral movement (rattling in the housing 80) arising when the main body unit 14 and the movable unit 15 perform the piston motion by the crank mechanism.

The main body unit 14 has a cylindrical shape. The main body unit 14 includes a first member 86 connected to the link 84, and a second member 87 connected to the first member 86. The first member 86 is connected to the link 84 via a connecting member 85. The first member 86 has an extending portion 86*a* extending inside the second member 87. The extending portion 86*a* includes the coil board 120 to which the receiving coil 11 is attached. The coil board 120 is disposed at a position opposed to the coil board 110 of the movable unit 15.

The second member 87 of the main body unit 14 has the movable unit 15. The movable unit 15 has a cylindrical shape. The movable unit 15 includes a first member 91 having the contact portion 20 to be in contact with the object, and a second member 92 connected to the first member 91 and disposed inside the second member 87 of the main body unit 14. The movable unit 15 is supported inside the second member 87 of the main body unit 14, with the contact portion 20 to be in contact with the object projecting out of a front end of the second member 87.

The spring 16 is disposed between the first member 91 of the movable unit 15 and a projecting portion 87*a* of the second member 87 of the main body unit 14. The second member 92 of the movable unit 15 includes the coil board 110 to which the transmitting coil 12 is attached. The coil board 110 is disposed at a position opposed to the coil board 120. Accordingly, the receiving coil 11 and the transmitting coil 12 are disposed so as to be opposed to each other. Also, the coil board 110 has the acceleration sensor 13 attached thereon.

As a characteristic of the present embodiment, a plurality of buffering members 93 are disposed on a periphery of the main body unit 14. By way of example, the buffering members 93 are rubber members. Each buffering member 93 is made of, for example, a silicone rubber. The buffering member 93 may be made of not a silicone rubber but a rubber used for a packing material, etc. In the example of FIG. 8, two buffering members 93 are disposed between the main body unit 14 and the housing 80. According to this configuration, even if the lateral movement (rattling in the housing 80) arises when the main body unit 14 and the movable unit 15 perform the piston motion by the crank mechanism, the buffering members 93 disposed between the main body unit 14 and the housing 80 can prevent the main body unit 14 from coming in contact with the housing 80. Preventing the main body unit 14 from coming in contact with the housing 80 enables the main body unit 14 and the movable unit 15 to perform smooth piston motion. Accordingly, this prevents noise from mixing in the information from the acceleration sensor 13, and as a result, accuracy of the hardness measured by the biometric durometer is improved.

From the viewpoint of preventing the main body unit 14 from coming in contact with the housing 80, it is sufficient if the buffering members 93 are disposed at at least two places on the periphery of the main body unit 14. Also, the buffering member 93 may be disposed against a part where the main body unit 14 is expected to come in contact with the housing 80.

Figure 10:
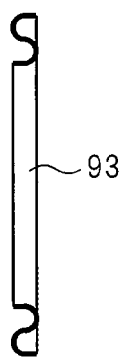
FIG. 10 is a side view of a buffering member according to the first embodiment.
Figure 11:
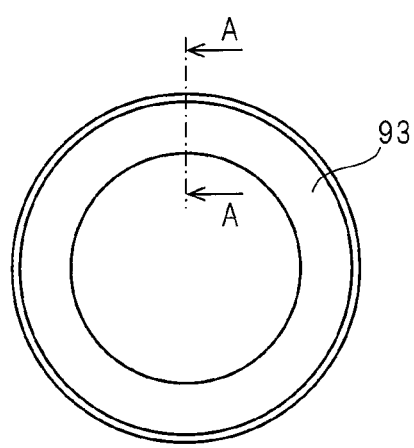
FIG. 11 is a diagram of the buffering member according to the first embodiment, when seen from a front side of the moving direction of piston motion.
Figure 12:
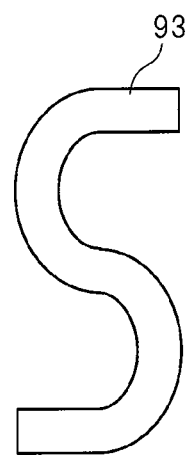
FIG. 12 is a cross-sectional view taken along a line A-A of FIG. 11.

FIGS. 10 to 12 each illustrate a structure of the buffering member 93. FIG. 10 is a side view of the buffering member 93, and FIG. 11 is a diagram of the buffering member 93, when seen from a front side of the moving direction of the piston motion. Also, FIG. 12 is a cross-sectional view taken along a line A-A of FIG. 11.

The buffering member 93 has a ring shape encircling the periphery of the main body unit 14 (FIG. 11). Also, the buffering member 93 has an S-shaped section (FIG. 12). This S-shaped section enables the buffering member 93 to have a spring property. Having the spring property, the buffering member 93 always returns to its original position easily when the main body unit 14 performs the piston motion. Accordingly, it is preferable that the buffering member 93 has the spring property in order to perform the stable piston motion, while having a function of preventing the main body unit 14 from coming in contact with the housing 80.

Figure 13:
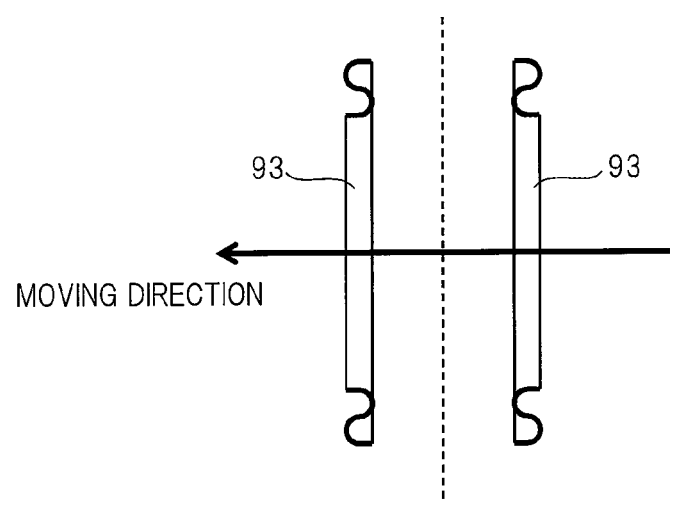
FIG. 13 is an example of preferred arrangement of the buffering members of the first embodiment.

FIG. 13 is an example of preferred arrangement of the buffering members 93. Two buffering members 93 are disposed such that their S-shapes face each other. In other words, the two buffering members 93 are disposed such that their S-shapes are symmetrical with each other with respect to a plane perpendicular to the moving direction (which is indicated by a dotted line in FIG. 13). When the main body unit 14 performs the piston motion, positions of the buffering members 93 may be shifted in the moving direction. In this manner, when the buffering members 93 are disposed such that their S-shapes face each other, it is possible to prevent the buffering member 93 from shifting when the main body unit 14 performs the piston motion.

Note that, although the buffering member 93 with an S-shaped section has been described in the example of FIGS. 10 to 13, the configuration of the buffering member 93, however, is not limited to this. The buffering member 93 may have a rectangular cross-sectional shape. When its spring property is taken into consideration, the buffering member 93 may have a cross-sectional shape having at least one curved part.

To prevent the buffering members 93 from shifting when the piston motion is performed, the main body unit 14 may have an antislip member 94 disposed on the periphery of the buffering members 93. By way of example, the antislip member 94 is a polyester tape (Mylar tape). It is sufficient if the antislip member 94 serves as an element forming a level difference on the main body unit 14, and the antislip member 94 may be made of a material different from the polyester tape.

Figure 14:
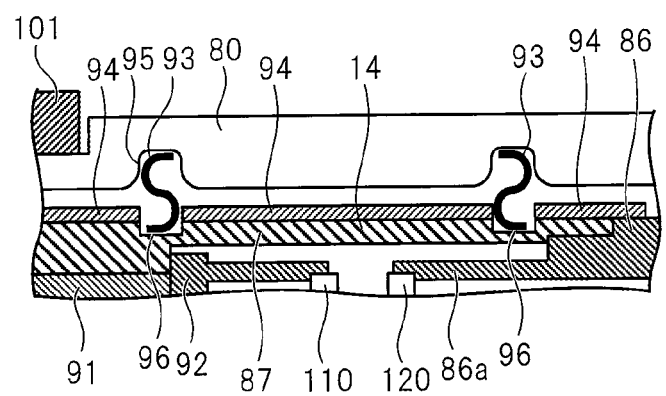
FIG. 14 is an enlarged view illustrating another configuration of the biometric durometer according to the first embodiment.

In the example of FIG. 8, the antislip member 94 is disposed between the two buffering members 93. The position of the antislip member 94 is, however, not limited to the position in this example. FIG. 14 is an enlarged view illustrating another configuration of the biometric durometer. As illustrated in FIG. 14, preferably, the antislip member 94 may be disposed in front of and behind each buffering member 93 in the moving direction.

Also, as illustrated in FIG. 14, the main body unit 14 may have groove portions 96 provided at positions corresponding to the buffering members 93. These groove portions 96 can prevent the buffering members 93 from shifting when the main body unit 14 performs the piston motion.

Also, as illustrated in FIG. 14, the housing 80 may have groove portions 95 provided at positions corresponding to the buffering members 93. These groove portions 95 can prevent the buffering members 93 from shifting when the main body unit 14 performs the piston motion.

Also, according to the present embodiment, the measurement apparatus 1 further includes a contact member (guard member) 101 encircling a periphery of the movable unit 15 and coming in contact with the object to be measured. The contact member 101 is cylindrical and is attached to a front end of the second portion 80b of the housing 80 with a screw 103.

The contact member 101 has a press portion 101a pressed against the object to be measured (FIG. 8). The relation between the press portion 101a of the contact member 101 and the contact portion 20 of the movable unit 15 will be described here. A surface of the contact portion 20 of the movable unit 15 and a surface of the press portion 101a of the contact member 101 are flush with each other when the surfaces are at the midpoint of the amplitude of the piston motion. At the peak of the amplitude of the piston motion, therefore, the surface of the contact portion 20 of the movable unit 15 projects forward from the surface of the press portion 101a of the contact member 101. By way of example, when the amplitude of the piston motion is 3 mm, the surface of the contact portion 20 of the movable unit 15 projects by 1.5 mm forward from the surfaces of the press portions 101a of the contact member 101 at the peak of the amplitude of the piston motion.

Figure 15:
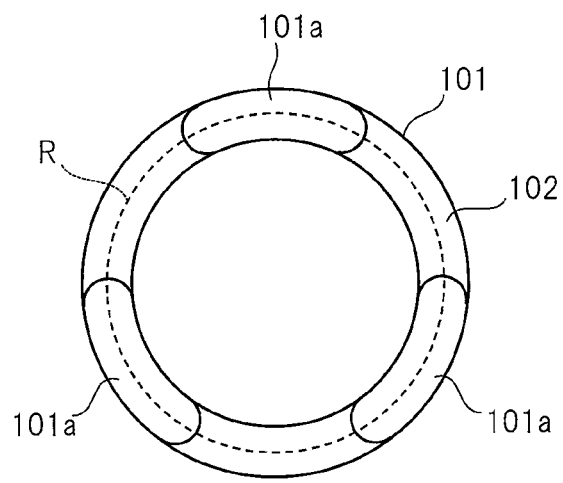
FIG. 15 is a diagram of a contact member according to the first embodiment, when seen from the front side of the moving direction of the piston motion.
Figure 16:
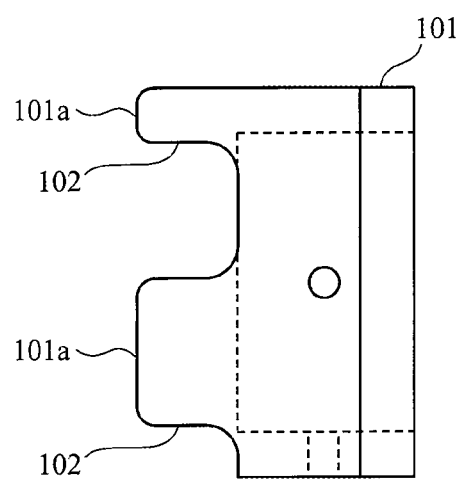
FIG. 16 is a side view of the contact member according to the first embodiment.

FIG. 15 is a diagram of a contact member 101, when seen from the front side of the moving direction of the piston motion, and FIG. 16 is a side view of the contact member 101. The contact member 101 has three press portions 101a. To form a single surface against the object to be measured, the contact member 101 needs to include at least three press portions 101a making up the single surface. According to this configuration, when the three press portions 101a are brought into contact with the object to be measured and the main body unit 14 performs the piston motion, the measurement apparatus 1 can be held at a certain position (height) relative to the object to be measured, and, at the same time, the contact portion 20 of the movable unit 15 can be brought into contact perpendicularly with the object to be measured. As a result, accurate hardness information can be obtained.

Also, the contact member 101 has three cutouts 102. For example, when the object to be measured is a human body, pressing the contact member 101 against the object to be measured causes skin surface to be hardened due to tension of the skin surface. When the skin surface becomes a hardened state in this manner, the original hardness of the skin or the muscle cannot be measured. In contrast, since the contact member 101 has the cutouts 102, the tension of the skin surface is released through the cutouts 102. Accordingly, the original hardness of the skin or the muscle can be measured.

Note that the number of cutouts 102 is not limited to three. Since the cutouts 102 serves the above mentioned function of releasing the tension of the skin surface, the cutouts 102 should preferably be provided in such a way as to occupy a wider area in the contact member 101. By way of example, it is preferable that, in a plan view (of the contact surface in contact with the object to be measured) in FIG. 15, the cutouts 102 occupy ½ or more of the circumference R of the contact member 101.

[Second Embodiment]

Figure 17:
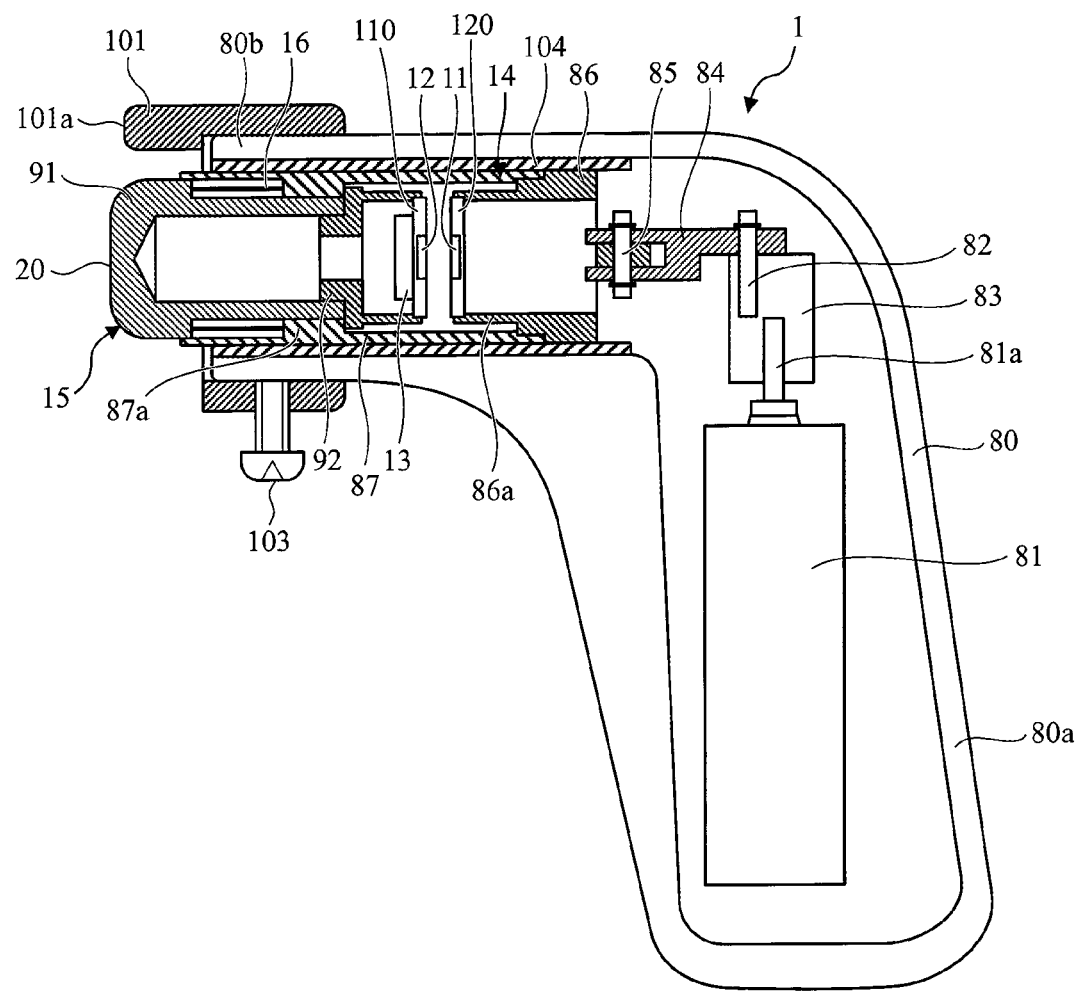
FIG. 17 is a configuration diagram of a biometric durometer according to a second embodiment.

FIG. 17 is a configuration diagram of a biometric durometer according to a second embodiment. The same constituent elements as described in the above embodiment will be denoted by the same reference characters, and the descriptions thereof are omitted.

A characteristic of the present embodiment is in that one buffering member 104 is disposed on the periphery of the main body unit 14. The buffering member 104 is disposed between the main body unit 14 and the housing 80. The buffering member 104 is a gelled member covering the periphery of the main body unit 14. For example, the buffering member 104 is a silicone gel. Further, the buffering member 104 may be provided as a bag of silicone gel or material equivalent thereto. Note that another gelled member different from the silicone gel may be used as the buffering member 104 from the viewpoint of preventing contact between the main body unit 14 and the housing 80.

FIG. 17 illustrates an example in which the buffering member 104 is disposed in such a way as to cover the entire periphery of the main body unit 14. A position of the buffering member 104, however, is not limited to the position illustrated in this example. For example, the buffering member 104 may be disposed only at a part where the main body unit 14 is expected to come in contact with the housing 80.

Figure 18:
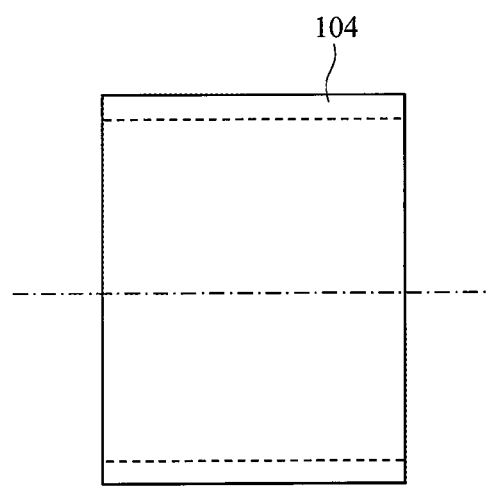
FIG. 18 is a side view of another example of the buffering member.
Figure 19:
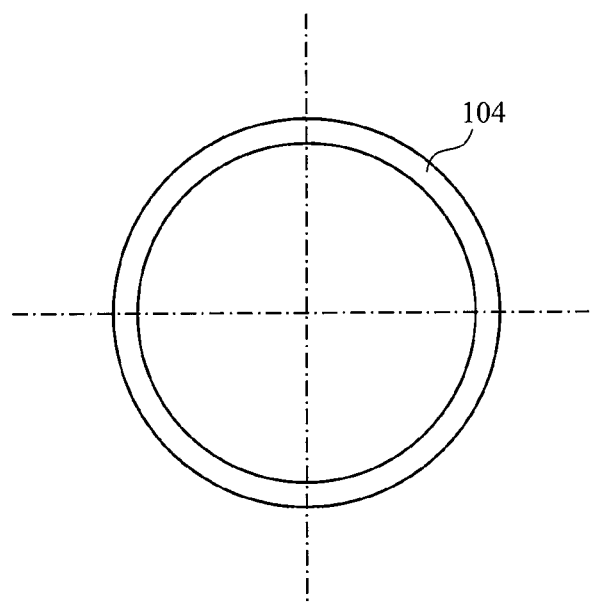
FIG. 19 is a diagram of the buffering member of FIG. 18, when seen from the front side of the moving direction of the piston motion.

A buffering member different from the above gelled buffering member may also be used. One or a plurality of resin or metal buffering members having a bearing structure may be used as the buffering member 104. The buffering member 104 having the bearing structure is made of, for example, Teflon. FIG. 18 is a side view of the resin or the metal buffering member 104 having the bearing structure, and FIG. 19 is a diagram of the buffering member 104 of FIG. 18, when seen from the front side of the moving direction of the piston motion. The buffering member 104 is cylindrical and is disposed on the periphery of the main body unit 14.

Also, the buffering member 104 may be a resin or a metal ring-shaped member. In this configuration, the ring-shaped buffering member 104 is disposed at one or a plurality of places on the periphery of the main body unit 14 where the main body unit 14 is expected to come in contact with the housing 80.

In the example illustrated FIGS. 18 and 19, it is preferable that, to reduce friction between an inner surface of the bearing structure (buffering member 104) and the main body unit 14, a contact surface of the buffering member 104 in contact with the main body unit 14 be subjected to the following surface treatment. For example, the contact surface of the buffering member 104 in contact with the main body unit 14 may be subjected to a mirror surface treatment (in the case of the metal buffering member 104, for example, the contact surface may be polished). Alternatively, the contact surface of the buffering member 104 in contact with the main body unit 14 may be subjected to a coating treatment. As such coating treatment, for example, silicon coating or Teflon coating is effective.

Figure 20:
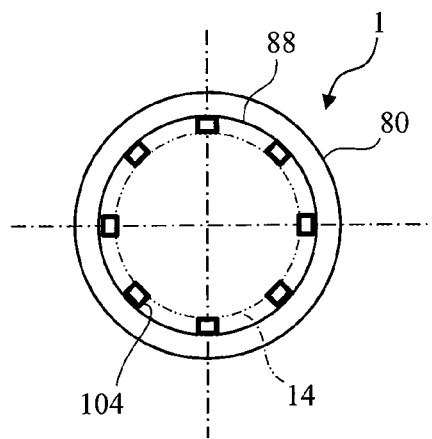
FIG. 20 is a diagram of another example of the buffering member, when seen from the front side of the moving direction of the piston motion.
Figure 21:
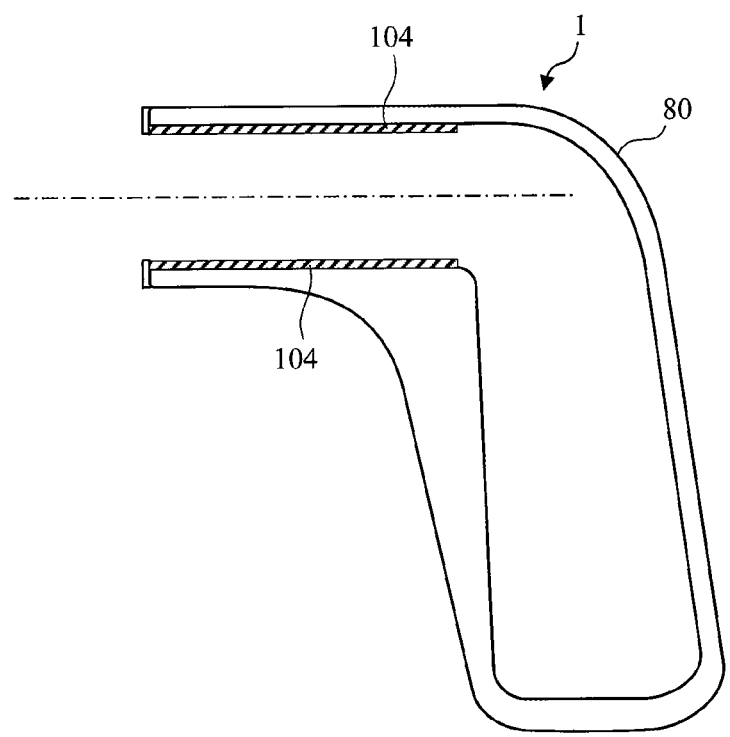
FIG. 21 is a cross-sectional view when the buffering member of FIG. 20 is disposed in the measurement apparatus.

A plurality of projections may be provided on an inner wall (inner surface) 88 of the housing 80, as the buffering members 104. FIG. 20 illustrates a configuration in which eight projecting bars (rib structures) are provided as the buffering members 104, illustrating a view of the buffering members 104, when seen from the front side of the moving direction of the piston motion of the main body unit 14. FIG. 21 is a cross-sectional view when the buffering member 104 of FIG. 20 is disposed in the measurement apparatus 1. As illustrated in FIG. 20, eight bar-like buffering members 104 are arranged at certain intervals on the periphery of the main body unit 14 (which is indicated by a virtual line). Also, as illustrated in FIG. 21, the eight bar-like buffering members 104 extend along the direction of the piston motion of the main body unit 14.

In an example in FIGS. 20 and 21, an example in which the eight bar-like buffering members 104 are arranged has been described. The plurality of projecting buffering members 104 are effective in such a structure as to reduce a contact area between the housing 80 and the main body unit 14 or to reduce a friction coefficient between the housing 80 and the main body unit 14.

The plurality of projecting buffering members 104 should be arranged in such a way as to support the periphery of the main body unit 14 (circumference of the main body unit 14) at least three points. When rattling arising as a result of the piston motion of the main body unit 14 and the movable unit 15 by the crank mechanism is taken into consideration, it is preferable that four or more projecting buffering members 104 be arranged on the periphery of the main body unit 14 (circumference of the main body unit 14).

In the example of FIG. 20, a section of each of the buffering members 104 (i.e., a section of the projection when seen from the front side of the moving direction of the piston motion) is rectangular but is not limited to this. The section of each of the buffering members 104 (i.e., a section of the projection) may be of other shapes such as a triangular or a semi-spherical shape. Also, since the buffering member 104 has the rectangular section and is formed to have the bar-like shape along the direction of the piston motion of the main body unit 14 in the example of FIGS. 20 and 21, the buffering member 104 is in surface contact with the main body unit 14. The configuration of the buffering member 104, however, is not limited to this. The projecting buffering member 104 may be in point or line contact with the main body unit 14, depending on its configuration such as the sectional shape of the buffering member 104. The contact surface of the projecting buffering member 104 in contact with the main body unit 14 may be subjected to the above-described coating.

Further, stability when the main body unit 14 and the movable unit 15 perform the piston motion by the crank mechanism is taken into consideration, and to ensure the stability, the main body unit 14 may have the groove portions provided at respective positions corresponding to the buffering members 104. For example, the plurality of groove portions (rail structures) extending along the direction of the piston motion of the main body unit 14 may be provided at the respective positions corresponding to the bar-like buffering members 104 on the periphery of the main body unit 14. According to this configuration, the rattling arising as a result of the piston motion of the main body unit 14 and the movable unit 15 by the crank mechanism can be prevented more effectively.

According to this configuration, even if the lateral movement (rattling in the housing 80) arises when the main body unit 14 and the movable unit 15 perform the piston motion by the crank mechanism, the buffering members 104 disposed between the main body unit 14 and the housing 80 can prevent the main body unit 14 from coming in contact with the housing 80. Preventing the main body unit 14 from coming in contact with the housing 80 enables the main body unit 14 and the movable unit 15 to perform smooth piston motion. Accordingly, it is possible to prevent noise from mixing in information from the acceleration sensor 13, and as a result, the accuracy of the hardness measured by the biometric durometer can be improved.

The present invention is not limited to the above-described embodiments, and various modifications are included. For example, the above-described embodiments have been described in detail so that the present invention is easily understood, and are not limited to the one necessarily including all configurations described. Also, a part of the configuration of an embodiment can be replaced with the configuration of other embodiments. Also, the configuration of other embodiments can be added to the configuration of an embodiment. In addition, other configurations can be added to, deleted from, or replaced with a part of the configuration of each embodiment.

A part or all of each processing of the microprocessor 23 described above may be realized by hardware, for example, by designing an integrated circuit. In addition, each configuration, function, etc. described above may be realized by software in which a processor interprets and executes a program realizing each function. Information such as a program realizing each function, a table, and a file may be stored on a recording device such as a memory, a hard disk, or a solid state drive (SSD), or a recording medium such as an IC card, an SD card, or a DVD.

A control line or an information line considered to be necessary for description is indicated in the above-described embodiments, and all the control lines or the information lines in the product are not necessarily indicated. All configurations may be mutually connected.

EXPLANATION OF REFERENCE CHARACTERS

1000 . . . Biometric durometer
1, 1a . . . Measurement apparatus
2 . . . Hardness calculation apparatus
11 . . . Receiving coil
12 . . . Transmitting coil
13 . . . Acceleration sensor (first sensor)
14 . . . Main body unit
15 . . . Movable unit
16, 16a . . . Spring
17(a) . . . Spring
17(b) . . . Dashpot
18 . . . Battery 19 ... Magnetic sensor (second sensor)
20 ... Contact portion
21, 22 ... Driving circuit
23 ... Microprocessor
24 ... Storage unit
25 ... Sound generation unit
26 ... Display unit
27 ... Power source unit
28 ... Input unit
31 ... AC oscillation source
32 ... Amplifier
33 ... Preamplifier
34 ... Detection circuit
35 ... Reference signal
36 ... Low-pass filter
80 ... Housing
81 ... Motor
82 ... Crank shaft
83 ... Bearing member
84 ... Link
85 ... Connecting member
86 ... First member of the main body unit
87 ... Second member of the main body unit
91 ... First member of the movable unit
92 ... Second member of the movable unit
93 ... Buffering member
94 ... Antislip member
95, 96 ... Groove portion
101 ... Contact member
101a ... Press portion
102 ... Cutout
104 ... Buffering member
110, 120 ... Coil board
130 ... Operating circuit board
190 ... Operation button
231 ... Differential waveform generation unit
232 ... Waveform comparison unit
233 ... Conversion coefficient calculation unit
235 ... Calculation unit
236 ... Determination unit

The invention claimed is:

1. A durometer comprising:
a main body unit including a movable unit pressed continuously against an object to be measured;
a housing housing the main body unit;
a first sensor outputting acceleration information corresponding to an acceleration of movement of a contact part of the object to be measured in contact with the movable unit in a pressing direction;
a second sensor outputting reactive force information corresponding to a reactive force at the contact part of the object to be measured in contact with the movable unit;
a motor;
a crank mechanism driven by the motor and causing the main body unit and the movable unit to perform piston motion; and
at least one buffering member disposed between a periphery of the main body unit and the housing.

2. The durometer according to claim 1,
wherein the at least one buffering member comprises at least two buffering members that are disposed at least two places between the periphery of the main body unit and the housing.

3. The durometer according to claim 2,
wherein the at least two buffering members have an S-shaped section.

4. The durometer according to claim 3,
wherein the at least two buffering members are arranged such that their S-shapes face each other.

5. The durometer according to claim 2,
wherein the at least two buffering members are a rubber member.

6. The durometer according to claim 1,
wherein the main body unit has a groove portion provided at a position corresponding to the at least one buffering member.

7. The durometer according to claim 1,
wherein the main body unit has an antislip member disposed on a periphery of the at least one buffering member.

8. The durometer according to claim 1,
wherein the second sensor includes two coils and a spring.

9. The durometer according to claim 1, wherein the housing further houses
the main body unit, the first sensor, the second sensor, the motor, the crank mechanism, and the at least one buffering member.

10. The durometer according to claim 9,
wherein the housing has a groove portion provided at a position corresponding to the at least one buffering member.

11. The durometer according to claim 1,
wherein the at least one buffering member is a gelled member covering the periphery of the main body unit.

12. The durometer according to claim 1, further comprising:
a contact member having a shape so as to encircle a periphery of the movable unit and in contact with the object to be measured,
wherein the contact member includes a press portion in contact with the object to be measured and a cutout that is cut out so as to not be in contact with the object to be measured, the press portion and the cutout being alternately arranged in a circumferential direction.

13. The durometer according to claim 12,
wherein the contact member is of a cylindrical shape, and the cutout occupies ½ or more of a circumference of the contact member when seen from a side of a contact surface in contact with the object to be measured.

14. The durometer according to claim 1,
wherein the crank mechanism includes:
a crank shaft located eccentric to a shaft of the motor; and
a connecting member connecting the crank shaft to the main body unit,
wherein a length of the connecting member is ⅓ or more of a length of the main body unit in a moving direction.

15. The durometer according to claim 1,
wherein the at least one buffering member comprises a plurality of buffering members comprising a resin or a metal cylindrical member, the plurality of buggering members being disposed at one or a plurality of places on the periphery of the main body unit.

16. The durometer according to claim 15,
wherein an inner surface of the cylindrical member is subjected to a coating or polishing treatment.

17. The durometer according to claim 9,
wherein the at least one buffering member comprises three buffering members, each buffering member comprising a projection formed on an inner surface of the housing.

18. The durometer according to claim 17, wherein each projection is formed in such a way as to extend along a direction of the piston motion of the main body unit.

19. A durometer comprising:
- a main body unit including a movable unit pressed continuously against an object to be measured;
- a housing the main body unit;
- a first sensor outputting acceleration information corresponding to an acceleration of movement of a contact part of the object to be measured in contact with the movable unit in a pressing direction;
- a second sensor outputting reactive force information corresponding to a reactive force at the contact part of the object to be measured in contact with the movable unit;
- a motor;
- a crank mechanism driven by the motor and causing the main body unit and the movable unit to perform piston motion;
- at least one buffering member disposed between a periphery of the main body unit and the housing; and
- a contact member having a shape so as to encircle a periphery of the movable unit and in contact with the object to be measured,
- wherein the contact member includes a press portion in contact with the object to be measured and a cutout that is cut out so as to not be in contact with the object to be measured, the press portion and the cutout being alternately arranged in a circumferential direction.

* * * * *